United States Patent [19]

Cromie

[11] 4,416,595
[45] Nov. 22, 1983

[54] MINIATURE ROTARY INFUSION PUMP WITH SLIDE LATCH AND DETACHABLE POWER SOURCE

[75] Inventor: Harry W. Cromie, Pittsburgh, Pa.

[73] Assignee: Baxter Travenol Laboratories, Inc., Deerfield, Ill.

[21] Appl. No.: 243,540

[22] Filed: Mar. 13, 1981

[51] Int. Cl.³ ............................................. F04B 43/12
[52] U.S. Cl. ..................................... 417/476; 418/45; 604/153; 128/DIG. 12; 429/96; 200/330
[58] Field of Search ........................ 417/476, 411, 477; 418/45; 128/214 F, 213 R, DIG. 12; 604/153

[56] References Cited

U.S. PATENT DOCUMENTS

| | | | |
|---|---|---|---|
| 2,414,355 | 1/1947 | Bogoslowsky | 103/149 |
| 2,679,807 | 6/1954 | Bruckmann | 103/149 |
| 2,818,815 | 1/1958 | Corneil | 103/149 |
| 3,109,383 | 11/1963 | Muller | 418/45 |
| 3,384,080 | 5/1968 | Muller | 128/214 |
| 3,508,546 | 4/1970 | Rogers et al. | 417/411 |
| 3,908,657 | 9/1975 | Kowarski | 128/214.4 |
| 3,927,955 | 12/1975 | Spinosa et al. | 417/477 |
| 4,006,743 | 2/1977 | Kowarski | 128/214 R |
| 4,008,717 | 2/1977 | Kowarski | 128/214 R |

FOREIGN PATENT DOCUMENTS

WO81/01728  6/1981  PCT Int'l Appl. ............... 417/477

Primary Examiner—Richard E. Gluck
Attorney, Agent, or Firm—John P. Kirby, Jr.; Garrettson Ellis; Bradford R. L. Price

[57] ABSTRACT

A pressure pump for fluid in which tubing is wound about an orbitally movable pressure member inside of a sleeve member which is defined by a pair of pivotally mounted, substantially semi-circular jaws to permit opening and closing of the jaws about the pressure member to facilitate installation of tubing. Sliding gripper means may be carried by the pump and positioned to interact in one position with grippable means on the free ends of the jaws to hold them in closed relation, and for the sliding gripper means to be moved to a second position to permit the jaws to open. Simultaneously, the sliding gripper means can serve as a latch for a lid of the casing in which the pump is carried. Also the casing may have a partition with groove means having an enlarged portion for receiving joined connectors in the tubing, and a power source such as a battery may be attached to a removable portion of the casing in such a manner as to prevent accidental reverse installation of the battery.

5 Claims, 12 Drawing Figures

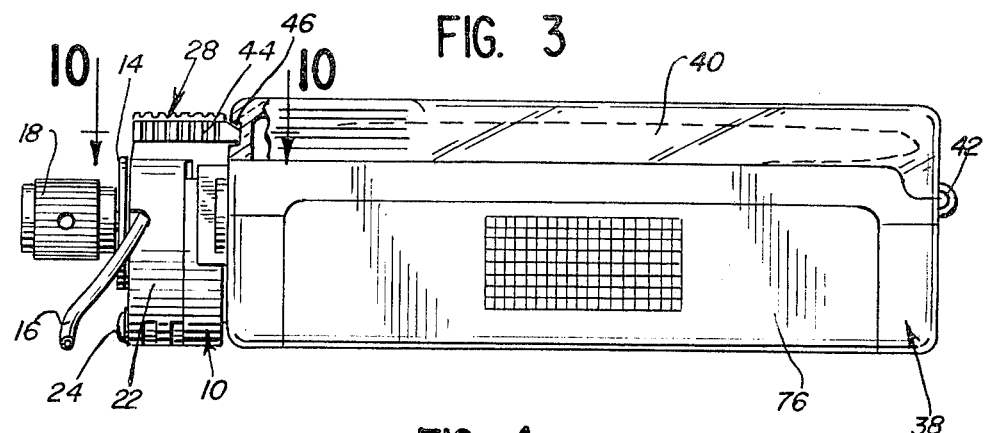
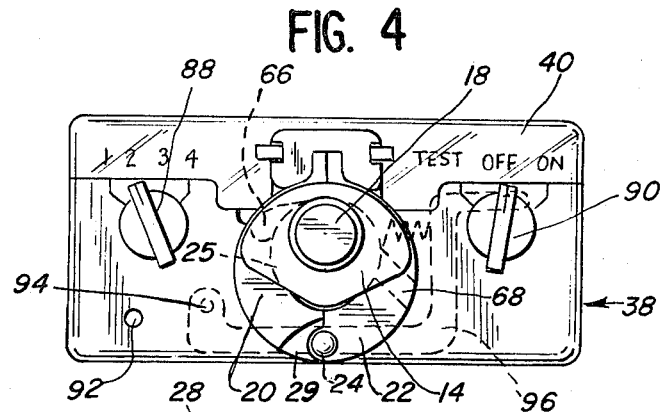
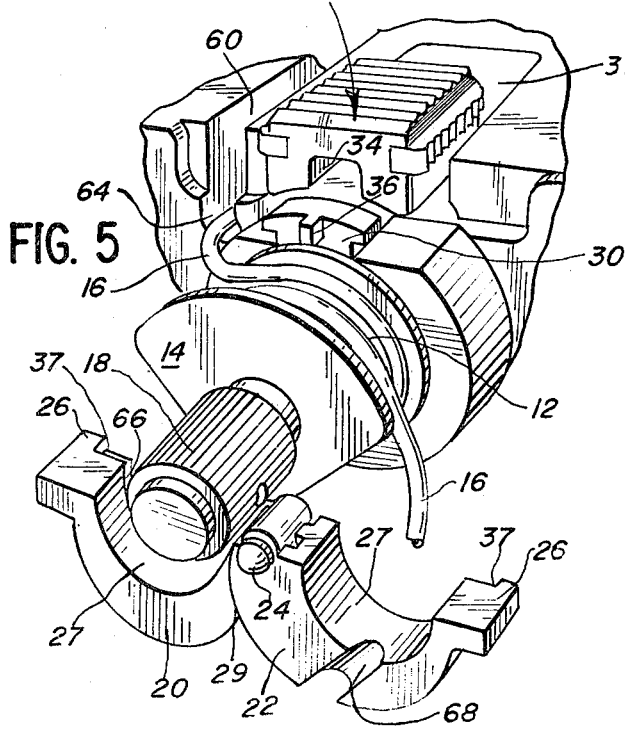
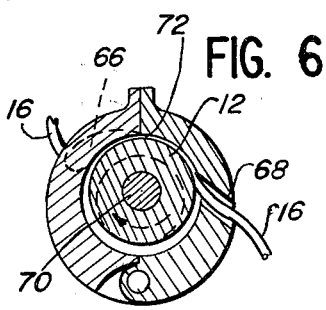
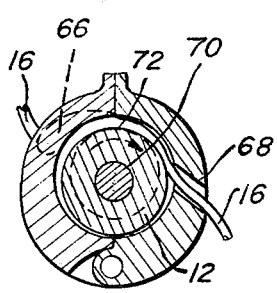

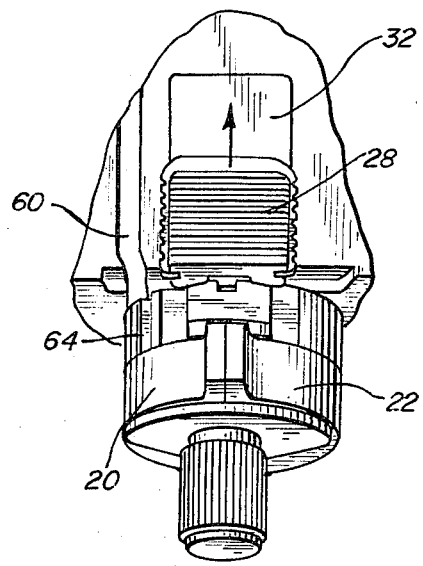
FIG. 8
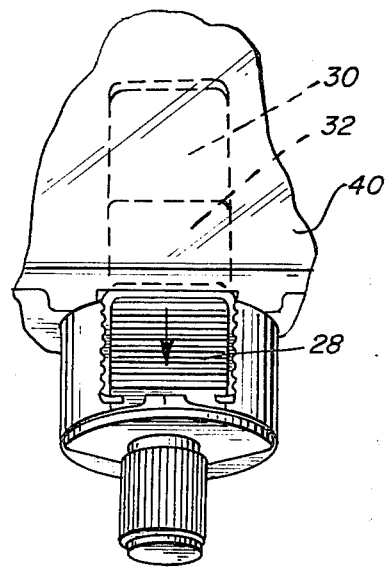
FIG. 9
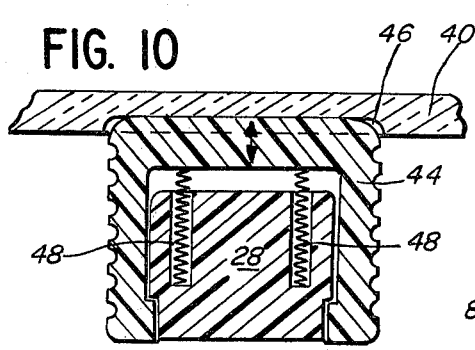
FIG. 10
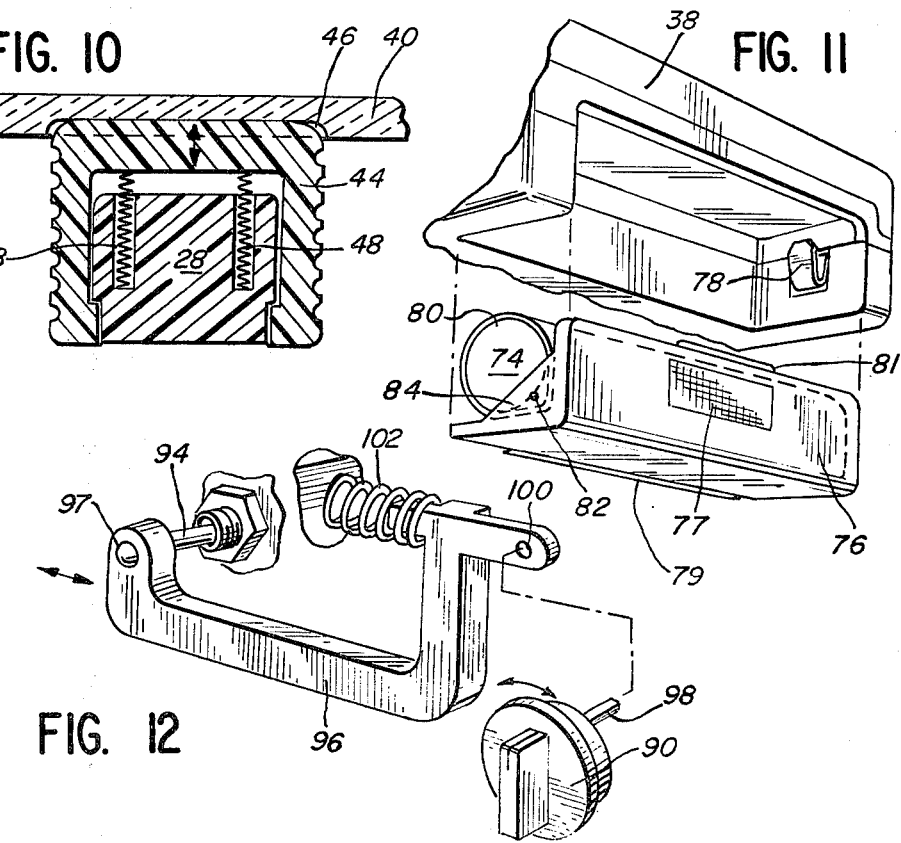
FIG. 11
FIG. 12

MINIATURE ROTARY INFUSION PUMP WITH SLIDE LATCH AND DETACHABLE POWER SOURCE

TECHNICAL FIELD

This application relates to wearable pumps for continuous medicament administration.

BACKGROUND ART

In U.S. Pat. No. 3,908,657, a small, wearable medical pump for fluids is disclosed. Also, wearable pumps which comprise a pressure member adapted for orbital motion about an axis of rotation to pump liquids through flexible tubing are commercially available, and may be worn for either the withdrawal of blood for medical purposes or for the controlled infusion of critical medications which should be administered in very low but constant concentrations on an all-day basis. Accordingly, the patient is able to engage in his normal activities while wearing such a pump.

Such a pump is manufactured by Cormed, Inc. of Middleport, N.Y. The pressure member adapted for orbital motion is surrounded by a rigid sleeve, which defines an annular groove in its end. The tubing for pumping is forced into the end groove for operation of the pump.

This, however, provides a substantial disadvantage in that the tubing is difficult to get into the groove and into engagement with the pump head or pressure member without being pushed in by a pointed instrument of some kind. This, in turn, can damage the tubing if not done carefully.

Also, the above-cited miniature pump defines a single side slot, into which the tubing enters and exits from the rigid sleeve which surrounds the pump head. At those times, when the pump head is positioned against the side slot, it is possible for liquids to flow through the tubing in an uncontrolled manner, since the side slot provides a position for the tubing sections to retreat from the pump head, and thereby not be closed by the head as in the normal mode of operation. Particularly, if by chance the pump head is stopped in a position against the slot, flow can take place in a free and uncontrolled manner through the tubing, which is most undesirable, particularly when a critical dosage of medicament is being administered.

In the Olson U.S. patent application Ser. No. 104,407, filed Dec. 17, 1979 and entitled "Miniature Infusion Pump", improvements to the above-described structure are disclosed. The orbitally movable pressure member is surrounded by a sleeve member which is defined by a pair of substantially semi-circular jaws, attached together at one end in hinged relation for ease of installation.

In accordance with this invention, further improvements are provided in an orbital motion tubing pump for ease of use. Particularly, the number of detachable parts is reduced at the pump head, to avoid accidental loss of a detachable part. Also, the loading of pump tubing connected to a bag filled with medicament is easier by the improvements of this invention, and additional features for convenience and improved safety are provided.

DISCLOSURE OF INVENTION

The invention relates to a pressure pump for fluids, through flexible tubing, which comprises a pressure member of generally circular periphery, means for moving the pressure member in orbital motion about an axis of rotation, and a sleeve member positioned about the pressure member and spaced for receiving and retaining the flexible tubing in a predetermined position between the pressure member and the sleeve member, with the tubing surrounding the pressure member.

The sleeve member may be divided into a pair of substantially semi-circular jaws attached together at one end in hinged relation, to permit opening and closing of the jaws about the pressure member to facilitate installation of the tubing.

In accordance with this invention, the jaws may each define grippable means adjacent their ends opposite to the one hinged end. Sliding gripper means are carried by the pump, with the gripper means being capable of gripping the opposite ends of the jaws and retaining them together in closed relation in a first sliding position, and releasing the jaws to permit them to open in a second sliding position of the gripper means.

Preferably, the jaws may carry outwardly projecting tab members at their opposite or outer ends, and the sliding gripper means defines a slot to receive and hold the tab members in abutting relationship in the first sliding position.

The gripper means may be carried in sliding slot means defined in the pressure pump. Also, the pressure pump may carry stop means to prevent the opposite ends of each jaw from pivoting to a position more than 180° from the hinged position of the jaws.

The pressure pump may be carried by a casing with a hinged lid, with the pressure member projecting from the casing. The sliding gripper means may carry spring latch means to releasably hold the lid in closed position when the gripper means is in its first sliding position. Thus, the gripper means provides a double function of holding the hinged jaws in closed position, and at the same time closing the lid by means of the spring latch means.

For safety purposes, it is preferred for the arrangement to prevent the sliding gripper means from moving out of its first position while the lid is closed. Thus the tubing surrounding the pressure member cannot be tampered with or readjusted without opening the lid, followed by moving the sliding gripper means to the second position, which permits opening of the hinged jaws.

The casing described above may also include a partition positioned within the casing and enclosing the pressure pump. The partition, in turn, may be enclosable by the lid in closed position. Groove means are defined in the partition for receiving a portion of the flexible tubing which wraps about the pressure member. The groove means preferably defines an enlarged portion for receiving joined connectors attached respectively to an end of the tubing and a source of fluid for pumping. Accordingly, when the connector is placed in the enlarged portion, it serves as a restraint or lock on the tubing so that it cannot be pulled forward in the preferred circumstance where the connectors are too large to pass through the narrower portion of the groove means. This frees a hand from holding the tubing, for other use during the loading of tubing and winding it around the pressure member.

The source of tubing for pumping is preferably a bag which may be positioned within the housing, and may occupy substantially the same area as the casing, so that it fits in the casing under the lid and yet is of maximum size within the casing to hold a maximum amount of liquid for administration.

Furthermore, the pressure member may define an outer flange to retain the tubing in position between the pressure member and jaws.

Preferably the pressure member engages in orbital motion but does not rotate about its own axis, to provide pumping action against the tubing without abrasion caused by the surface of the pressure member rubbing against the tubing by rotation.

Further in accordance with this invention, the apparatus of this invention is powered by at least one battery. The apparatus and battery are carried within a casing, for example a casing similar to that described above. The casing defines a removable portion capable of attachment in only a single position. The battery is permanently secured to the removable casing. For example, the battery may define a jacket which, in turn, defines a longitudinally oriented passageway through the jacket, and a rod member attached at both ends to the removable portion of the casing extending through the passageway, to permanently secure the battery to the removable portion.

As the result of this, upon the reattachment of the casing portion to the rest of the casing in its only possible way, the battery is necessarily properly positioned between electrical contacts carried by the casing, without the possibility of an accidental reverse installation of the battery.

A major contemplated use of the pressure pump of this invention relates to the administration of medications in critical dosages to patients. The use of an attached battery of the type described helps to serve as a quality control aid as well as a means for preventing the user, who is likely to be an unwell or old person, from inserting the batteries in backwards. Also, it may be desired to use high quality batteries having different characteristics from those sold in a drug or hardware store, and the structure of this invention encourages the user to utilize only the authorized batteries for the system, which may be sold, each attached to a separate casing portion which is capable of attachment to the rest of the casing in only a single position.

Preferably, the removable portion of the casing to which the battery is attached comprises portions of at least two joined sides of the casing positioned in angular relation to each other.

Also, improvements to the switch system of the device of this invention and other improvements are as disclosed below.

BRIEF DESCRIPTION OF DRAWINGS

FIG. 3 is a side elevational view of the pressure pump and casing of FIG. 1, showing the lid in closed position.

FIG. 4 is an end elevational view of the pressure pump and casing as shown in FIG. 3. p FIG. 5 is a fragmentary, enlarged perspective view of the pressure member, jaws, and gripper means of the pressure pump as disclosed in the previous drawings.

FIG. 6 is a transverse sectional view taken through the pressure member, with the jaws shown in closed position.

FIG. 7 is a view similar to FIG. 6 with the pressure member shown in a different orbital position.

FIG. 8 is a fragmentary, perspective view of the jaws and sliding gripper means with the jaws shown in closed position, the gripper means in its second position, and the lid in open position.

FIG. 9 is a perspective view similar to FIG. 8 but with the sliding gripper means shown in its first position and the lid in closed position.

FIG. 10 is a fragmentary longitudinal sectional view of the handle of the sliding gripper means taken along line 10-10 of FIG. 3, showing the operation of the spring latch means for retaining the lid.

FIG. 11 is a detailed perspective view showing the separable portion of the casing and the attached battery, and how it may be attached to the remainder of the casing.

FIG. 12 is a detailed perspective view, with many portions removed, of part of the control system at the front of the casing.

DESCRIPTION OF SPECIFIC EMBODIMENT

Figure 1:
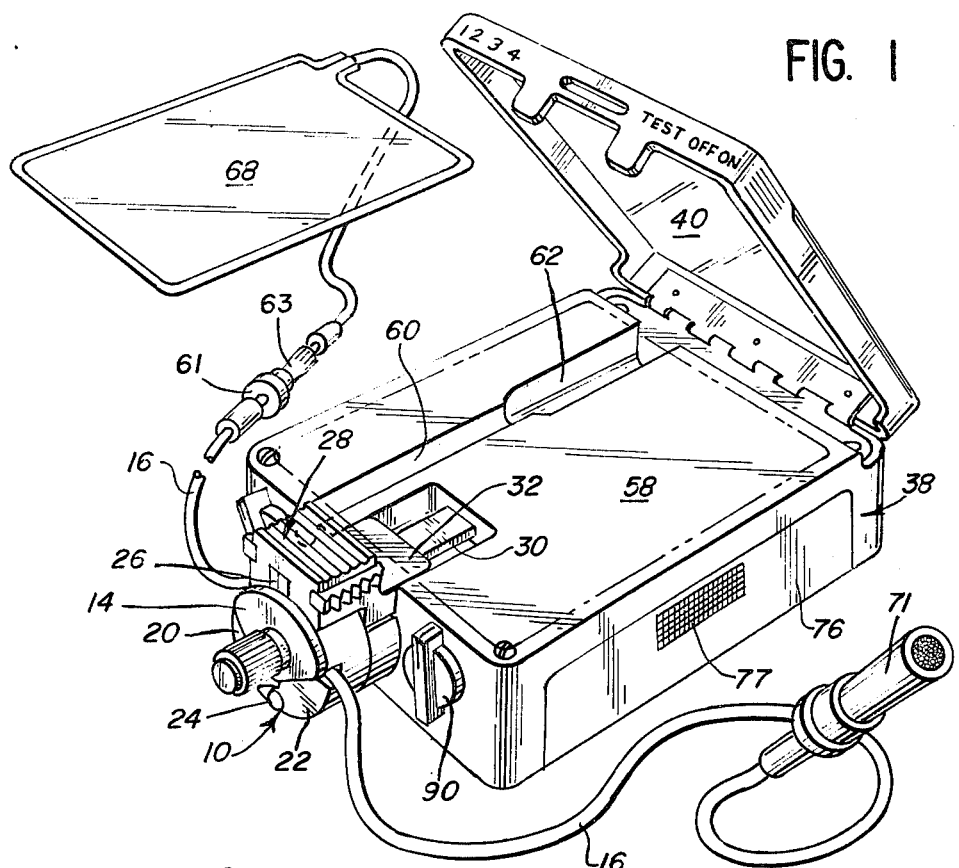
FIG. 1 is a perspective view of the pressure pump and casing in accordance with this invention.

Referring to the drawings, a pressure pump 10 for fluids passing through flexible tubing is provided which comprises a pressure member 12 (FIGS. 5 to 7) having an attached flange 14 on its outer end, and adapted, for example as shown in the previously-cited Olson patent application, or another conventional manner, for orbital motion about an axis of rotation, preferably in such a manner that the surface of pressure member 12 engages in orbital motion but does not rotate. Thus the length of tubing 16 which may be coiled around it as shown in FIG. 5 avoids rubbing between the surfaces of pressure member 12 and tubing 16.

Handle 18 permits manual movement of pressure member about its orbital path of rotation in one direction, while conventional means are utilized to prevent the backward rotation of orbital member 12.

Generally semicircular jaws 20, 22 are pivotally mounted together at one end by hinge 24 so that they may alternatively occupy an open position as shown in FIG. 5 to facilitate the winding and unwinding of tubing 16 about the pressure member, and alternatively may occupy a closed position as shown in FIG. 1, for example to define a sleeve member for receiving and retaining the flexible tubing 16 in a predetermined position between pressure member 12 and the sleeve member defined by jaws 20, 22 in their closed position.

Aperture 25 (FIG. 4) defined by the concave surfaces 27 of each jaw member 20, 22 may be a circular aperture surrounding pressure member 12 when the jaws are in closed position. Preferably, the circular aperture 25 is positioned off-center from the axis of the outer periphery of jaws 20, 22, being spaced slightly away from hinge 24 to provide more room for pivoting structure in the jaws adjacent hinge 24.

Cut-away portion 29 is provided in jaw 20 to permit wide opening of the jaws as shown in FIG. 5.

Figure 2:
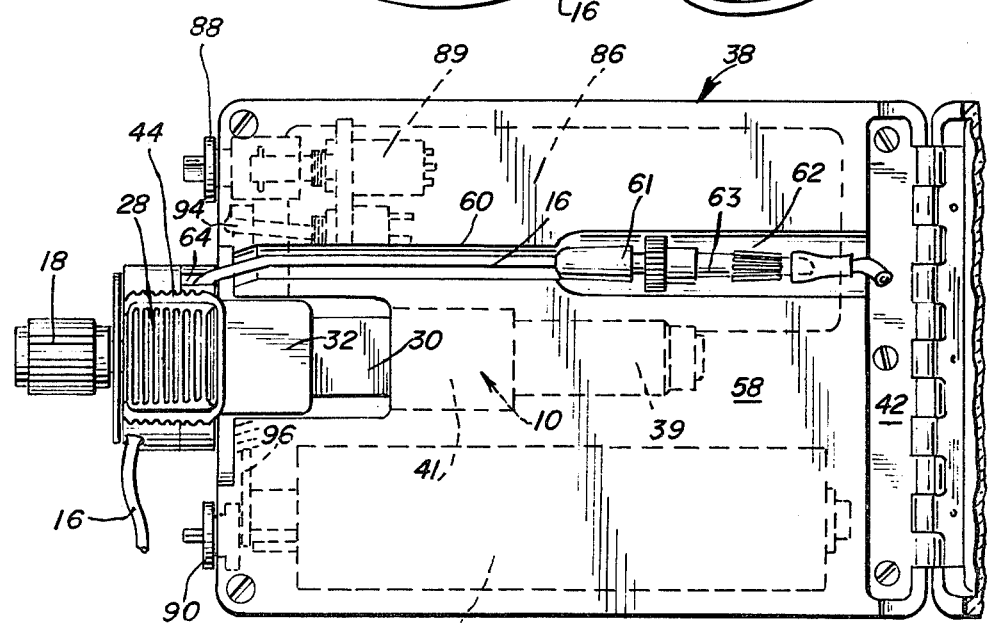
FIG. 2 is a plan view of the pressure pump and casing of FIG. 1, with the lid portion of the casing broken away.

Each of jaws 20, 22 define grippable means such as tab members 26. Furthermore, sliding gripper means such as gripper 28 is provided, carried by pump 10 on a sliding track 30 which engages rear portion 32 of gripper 28, permitting gripper 28 to be manually moved between a first sliding position as shown in FIGS. 1 and 2, and a second sliding position as shown in FIG. 5.

In the first sliding position, gripper 28 retains within its slot 34 the tab members 26 of jaws 20 and 22 in abutting relationship to hold the jaws in their closed position. In the second sliding position of gripper member 28, it can be seen that slot 34 is moved away from engagement with tabs 26, permitting the jaws to open as shown in FIG. 5. Thus the jaws 20, 22 may be easily opened by appropriate sliding of gripper member 28 to its second position, and to firmly and reliably remain closed by bringing the jaws together and then sliding gripper 28 to its first position.

The pressure pump 10 also carries stop means 36 (FIG. 5) which abuts against each tab 26 when the tabs 26 of the jaws are pivoted to a position which is essentially 180° from hinge 24, so that the jaws may avoid overpivoting in one direction or the other, which can interfere with the closing of gripper means 28 and locking of the jaws. Cut-away portions 37 are provided in the jaws so they can be closed in abutting relation, enclosing stop means 36.

Pump 10 may be carried by a casing 38 with a lid 40 which is attached to the remainder of casing 38 by hinge 42. As shown, the pressure member 12 and jaws 20, 22 of pump 10 may project from casing 38, while the motor 39 and gear box 41 are positioned inside casing 38.

Gripper member 28 may carry a spring latch 44, which is adapted to engage groove 46 in the front end of lid 40, to releasably hold lid 40 in its closed position when gripper means 28 is in its first sliding position. As can be seen, when gripper 28 is in its second sliding position, the lid 40 may be designed to not close or not be latchable.

As shown in FIG. 10, spring latch 44 may be an essentially U-shaped structure positioned about the horizontal edges of gripper member 28 and biased by a pair of springs 48 mounted in gripper member 28 outwardly. Thus, when it is desired to open lid 40, one can merely pull spring latch 44 forwardly toward handle 18 (FIG. 3) to cause it to withdraw from groove 46 so that the lid 40 may be opened. After lid 40 is opened, gripper member 28 may be moved from its first to its second position to permit jaws 20, 22 to be opened. This provides a positive opening procedure that makes it difficult to accidentally open the jaws in such a manner as to dislodge tubing 16, yet it is perfectly easy to open the jaws when access is desired.

In accordance with this invention, casing 38 carries a partition 58 positioned therein, enclosing a substantial portion of pressure pump 10 and, in turn, being enclosable by lid 40 in the closed position. A groove 60 is defined in partition 58 to receive tubing 16, which is threaded around pressure member 12 for pumping fluids therethrough. Groove 60 also defines an enlarged portion 62 positioned relatively remotely from jaws 20, 22 and pressure member 12, and proportioned to receive joined connectors 61, 63 attached respectively to an end of tubing 16 and a bag 68, which comprises the source of fluid for pumping. Accordingly, connectors 61, 63 may be placed in enlarged portion 62 of groove 60, and bag 68, which may be proportioned to be essentially of the same size as casing 38, may be placed on partition 58 so that it can be enclosed within the closed lid 40.

After this, since connector 61 cannot fit into the narrower portion of groove 60, one may simply pull on tubing 16, and connector 61 serves as a wedging lock for the upstream portion of tube 16, freeing a hand for easier installation of the tubing 16 into the pump head comprising pressure member 12 and jaws 20, 22. Tubing 16 may be threaded through open slot 64 in pump 10, and from there into inner circumferential slot 66, which is a cut-away portion on the inner circumference of jaw 20 which does not necessarily extend through to the outer surface of the jaw, but is in registry with slot 64 when jaw 20 is in the closed position, and permits tubing 16 therein to be guided into a circumferential winding around pressure member 12.

As shown in FIG. 5, tubing 16 then is wound around pressure member 12 typically about 1¼ turns, spiraling forwardly toward handle 18 as it proceeds, and then passes out of the pump head through slot 68 of jaw 22 as shown in FIGS. 5 through 7. From there, tubing 16 can terminate in a connector 71 which may be connected to a catheter of a patient, an IV needle, or the like for connection to the venous system of the patient, or merely inserted into the tissue, for administration of a critical medication such as insulin, a cancer chemotherapeutic agent, or some other medicament on a continuous, critical, low dosage basis.

Outer flange 14 serves to retain tubing 16 to prevent it from migrating out from between jaws 20, 22 and pressure member 12 during operation.

As illustrated in FIGS. 6 and 7, pressure member 12 rotates on a crank pin 70, with pressure member 12 being in freely rotating relationship relative to crank pin 70 and restrained in a manner similar to that disclosed in the Olson patent application cited above, so that individual portions 72 of the surface of pressure member do not rotate. As shown in the drawings, portion 72 of the surface remains in essentially the same rotational position, as orbital motion is produced on pressure member 12 by the rotation of crank 70.

The apparatus of this invention may be powered by a battery 74 which in many circumstances may be a high performance battery for improved reliability of operation, so that it may be undesirable for conventional drug store batteries or the like to be used in the apparatus.

In accordance with this invention, to insure the use of proper batteries in the device, and also to prevent the accidental reverse installation of the battery, the following structure may be utilized. It is considered particularly important to deter the user from the use of low quality batteries or accidental installment of the batteries backwards, since the users of the apparatus of this invention may be ill people or others who are not able to concentrate well and are likely to make an error.

Accordingly, by this invention the casing 38 may define a removable portion 76, which may be a simple snap-in section comprising at least two joined sides of the casing positioned in angular relation to each other. Roughened finger grip area 77 may also be provided with conventional detent type connection members 79, 81 (FIG. 11) for attachment of removable portion 76 to the casing 38.

As shown in FIG. 11, removable section 76 carries battery 74 in permanently secured relation to the removable portion. As the result of this, upon attachment of section 76 to casing 38, battery 74 may be properly positioned between electrical contacts 78 carried by the casing without the possibility of accidental reverse installation of the battery, because removable portion 76 is designed to be attachable to casing 38 in only a single position, i.e., the correct position of installation with respect to battery 74. This can be accomplished by making detent members 79, 81 and the mating channels in casing 38 to receive them, of differing lengths, or any other conventional means.

The term "permanent retention" is intended to include any form of normal retention between the battery and the casing portion 76 in such a circumstance where the battery cannot be easily or nondestructively separated from the casing portion, so that the user cannot easily mount drug store batteries or the like into the device of this invention. The batteries for use in this device may be manufactured, each attached to a separate removable casing portion, which may be quite inexpensively molded, the batteries 74 being sold in permanently attached relation to the casing portion 76.

Specifically, battery 74 defines a jacket 80 which, in turn, defines a longitudinally oriented passageway through jacket 80. A rod member 82, attached at both ends to removable casing portion 76, and specifically to side walls 84, extends through the passageway, to permanently secure the battery to removable portion 76.

The electronic circuitry 86 typically including a circuit board, may be of conventional design, although it may also include the circuit design as disclosed in the copending U.S. patent application of Gary Feldman, Ser. No. 243,539, filed concurrently herewith and entitled "Voltage Regulator". Speed control 88 may be connected to a conventional rotary switch member, with the speed being controlled by a resistance in the circuit which varies with each position of speed control 88.

Control 90 may be a three-way switch with respective off, on, and test positions. The test position causes light 92 to illuminate in the event that the voltage of battery 74 remains within desired operating specifications.

In the specific embodiment shown, a three-position toggle switch 94 is provided with appropriate connection to the circuitry for providing the off, on, and test modes.

A connector bar 96 of anodized aluminum is attached to toggle switch 94 by extension through aperture 97, as shown particularly in FIG. 12. Switch 90 has a projecting member 98 which is connected through an aperture 100 in connector bar 96. Accordingly, as switch 90 is rotated between its three positions, toggle 94, on the other side of the casing 38, is appropriately positioned.

Spring member 102 is positioned to bias switch 90 and toggle 94 away from the test position so that switch 90 and toggle 94 automatically spring back to the off position from the test position when manually released, for saving of electrical power.

Accordingly, switch 90 may be positioned remotely from the actual operation toggle switch 94, for ease of use and to eliminate crowding of the placement of the controls of the device of this invention.

The infusion device of this invention thus has numerous features of reliability, and convenience of use, so that it may be used by unskilled or substantially ill patients with safety and with continuously effective operation.

The above has been offered for illustrative purposes only, and is not intended to limit the scope of the invention of this application, which is as defined in the claims below.

That which is claimed is:

1. In a pressure pump for fluids through flexible tubing which comprises a pressure member of generally circular periphery, means for moving said pressure member in orbital motion about an axis of rotation, and a sleeve member positioned about said pressure member and spaced for receiving and retaining the flexible tubing in a predetermined position between the pressure member and the sleeve member with the tubing surrounding said pressure member, the sleeve member being divided into a pair of substantially semi-circular jaws attached together at one end in hinged relation to permit opening and closing of the jaws about the pressure member to facilitate installation of the tubing, the improvement comprising, in combination:

said jaws each defining grippable means comprising outwardly projecting tab members adjacent their ends opposite said one end, and sliding gripper means carried in sliding slot means defined in said pressure pump, said sliding gripper means defining a slot to receive said tab members in abutting relationship and carried by said pump, said gripper means being capable of gripping the opposite ends of the jaws and retaining them together in closed relation in a first sliding position and releasing said jaws to permit them to open in a second sliding position.

2. The pressure pump of claim 1 in which said pressure pump carries stop means to prevent the opposite ends of each jaw from pivoting to a position more than 180° from the hinge position of said jaws.

3. The pressure pump of claim 1 in which said pressure member defines an outer flange to retain said tubing in position between said pressure member and said jaws.

4. In a pressure pump for fluids for flexible tubing which comprises pressure member of generally circular periphery, means for moving said pressure member in orbital motion about an axis of rotation, and a sleeve member positioned about said pressure member and defining channel means for receiving and retaining the flexible tubing in a predetermined position between the pressure member and the sleeve member with the tubing surrounding said pressure member, the sleeve member being divided into a pair of substantially semi-circular jaws attached together at one end in hinged relation to permit opening and closing of the jaws about the pressure member to facilitate installation of the tubing, the improvement comprising, in combination:

said jaws each defining grippable means adjacent their ends opposite said one end, and sliding gripper means carried by said pump, said gripper means being capable of gripping the opposite ends of the jaws and retaining them together in closed relation in a first sliding position and releasing said jaws to permit them to open in a second sliding position, said gripper means being carried in sliding slot means defined in the pressure pump, said pressure pump being carried by a casing with a hinged lid, with said pressure member projecting from said casing, said sliding gripper means carrying spring latch means to releasably hold said lid in closed position which said gripper means is in its first sliding position.

5. In a pressure pump for fluids through flexible tubing which comprises a pressure member of generally circular periphery, means for moving said pressure member in orbital motion about an axis of rotation, and a sleeve member positioned about said pressure member and spaced for receiving and retaining the flexible tubing in a predetermined position between the pressure member and the sleeve member with the tubing surrounding said pressure member, the sleeve member being divided into a pair of substantially semi-circular jaws attached together at one end in hinged relation to permit opening and closing of the jaws about the pressure member to facilitate installation of the tubing, the improvement comprising, in combination:

said jaws each defining grippable means comprising outwardly projecting tab members adjacent their ends opposite said one end, and sliding gripper means defining a slot to receive said tab members in abutting relationship and carried by said pump, said pump being carried by a casing with a hinged lid, with said pressure member projecting from said casing, said gripper means being capable of gripping the opposite ends of the jaws and retaining them together in closed relation in a first sliding position and releasing said jaws to permit them to open in a second sliding position, said sliding gripper means carrying spring latch means to releasably hold said lid in closed position when said gripper means is in its first sliding position.

* * * * *